US012608803B2

(12) United States Patent
Madan et al.

(10) Patent No.: US 12,608,803 B2
(45) Date of Patent: Apr. 21, 2026

(54) MULTITHREADING VIDEO PROCESSING WITH CLOUD SERVICES TO DETECT AND ANALYZE LANDMARKS AND OBJECTS DURING A CLINICAL PROCEDURE

(71) Applicant: UTECH PRODUCTS, INC., Schenectady, NY (US)

(72) Inventors: Rakesh Madan, Schenectady, NY (US); Zohair Hussain, Schenectady, NY (US)

(73) Assignee: UTECH PRODUCTS, INC., Schenectady, NY (US)

( * ) Notice: Subject to any disclaimer, the term of this patent is extended or adjusted under 35 U.S.C. 154(b) by 0 days.

(21) Appl. No.: 19/027,716

(22) Filed: Jan. 17, 2025

(65) Prior Publication Data

US 2025/0157036 A1      May 15, 2025

Related U.S. Application Data

(63) Continuation-in-part of application No. 17/938,355, filed on Oct. 6, 2022, now Pat. No. 12,236,499.
(Continued)

(51) Int. Cl.
*G06T 7/00* (2017.01)
*A61B 1/00* (2006.01)
(Continued)

(52) U.S. Cl.
CPC ...... *G06T 7/0012* (2013.01); *A61B 1/000096* (2022.02); *A61B 1/00016* (2013.01);
(Continued)

(58) Field of Classification Search
None
See application file for complete search history.

(56) References Cited

U.S. PATENT DOCUMENTS 10,769,781 B2   9/2020   Chen et al.
11,132,794 B2   9/2021   Zur
(Continued)

FOREIGN PATENT DOCUMENTS

CN      114841952 A    8/2022
WO      2016057960 A1   4/2016
WO      2022050227 A1   3/2022

OTHER PUBLICATIONS

Zhang, Zijian et al.; "Asynchronous in Parallel Detection and Tracking (AIPDT): Real-Time Robust Polyp Detection"; AIPDT; Copyright Springer Nature Switzerland AG 2020; MICCAI 2020; LNCS 12263; pp. 722-731.
(Continued)

*Primary Examiner* — Frank Johnson
(74) *Attorney, Agent, or Firm* — Hoffman Warnick LLC

(57) ABSTRACT

A system and method for processing a video stream captured during a clinical procedure. A method includes receiving image data from a scope during a procedure; forwarding the image data to a display as the scope is inserted into a patient; forwarding the image data to a cloud service to identify a landmark in the image data using a first machine learning model; receiving landmark details from the cloud service in response to a detected landmark and outputting the image data with landmark annotations; receiving and forwarding further image data to the display as the scope is further manipulated within the patient; forwarding the further image data to a cloud service that is configured to detect lesions using a second machine learning model; and receiving lesion details from the cloud service in response to a detected lesion and outputting the further image data with lesion annotations via the display.

20 Claims, 8 Drawing Sheets

Related U.S. Application Data

(60) Provisional application No. 63/362,841, filed on Apr. 12, 2022.

(51) Int. Cl.

| | | |
|---|---|---|
| *A61B 1/31* | (2006.01) | |
| *G06V 20/40* | (2022.01) | |
| *G16H 50/20* | (2018.01) | |

(52) U.S. Cl.

CPC .......... *A61B 1/0002* (2013.01); *A61B 1/0005* (2013.01); *A61B 1/31* (2013.01); *G06V 20/41* (2022.01); *G16H 50/20* (2018.01); *G06T 2207/10016* (2013.01); *G06T 2207/10068* (2013.01); *G06T 2207/30028* (2013.01); *G06T 2207/30096* (2013.01); *G06V 2201/03* (2022.01)

(56) References Cited

U.S. PATENT DOCUMENTS

| | | | |
|---|---|---|---|
| 2002/0199000 A1* | 12/2002 | Banerjee | H04L 69/162 |
| | | | 709/227 |
| 2008/0091065 A1* | 4/2008 | Oshima | H04N 19/60 |
| | | | 382/128 |
| 2009/0036902 A1 | 2/2009 | DiMaio et al. | |
| 2012/0071710 A1* | 3/2012 | Gazdzinski | A61B 8/12 |
| | | | 600/101 |
| 2012/0214137 A1 | 8/2012 | Goree et al. | |
| 2013/0047074 A1* | 2/2013 | Vestergaard | H04N 21/44004 |
| | | | 715/234 |
| 2013/0332597 A1* | 12/2013 | Kumar | H04L 67/1029 |
| | | | 709/224 |
| 2016/0325680 A1* | 11/2016 | Curtis | H04W 4/024 |
| 2017/0061608 A1 | 3/2017 | Kim et al. | |
| 2019/0080454 A1 | 3/2019 | Hameed et al. | |
| 2019/0164518 A1 | 5/2019 | Dimitrov | |
| 2019/0206562 A1* | 7/2019 | Shelton, IV | H04N 23/555 |
| 2019/0307321 A1* | 10/2019 | Ikuta | G01J 3/18 |
| 2020/0364088 A1 | 11/2020 | Ashwathnarayan et al. | |
| 2020/0387706 A1* | 12/2020 | Zur | G06T 7/0012 |
| 2021/0161363 A1 | 6/2021 | Makino | |
| 2021/0280312 A1* | 9/2021 | Freedman | G16H 30/40 |
| 2022/0230311 A1 | 7/2022 | Zhang et al. | |
| 2022/0319708 A1* | 10/2022 | Hart | G06T 7/0012 |
| 2023/0043645 A1* | 2/2023 | Protsenko | A61B 1/31 |
| 2023/0100302 A1 | 3/2023 | Asai et al. | |
| 2023/0277249 A1 | 9/2023 | Bork et al. | |

OTHER PUBLICATIONS

International Search Report and the Written Opinion mailed Jan. 26, 2023 for PCT/US2022/077647 filed Oct. 6, 2022; 11 Pages.

* cited by examiner

Figure 4

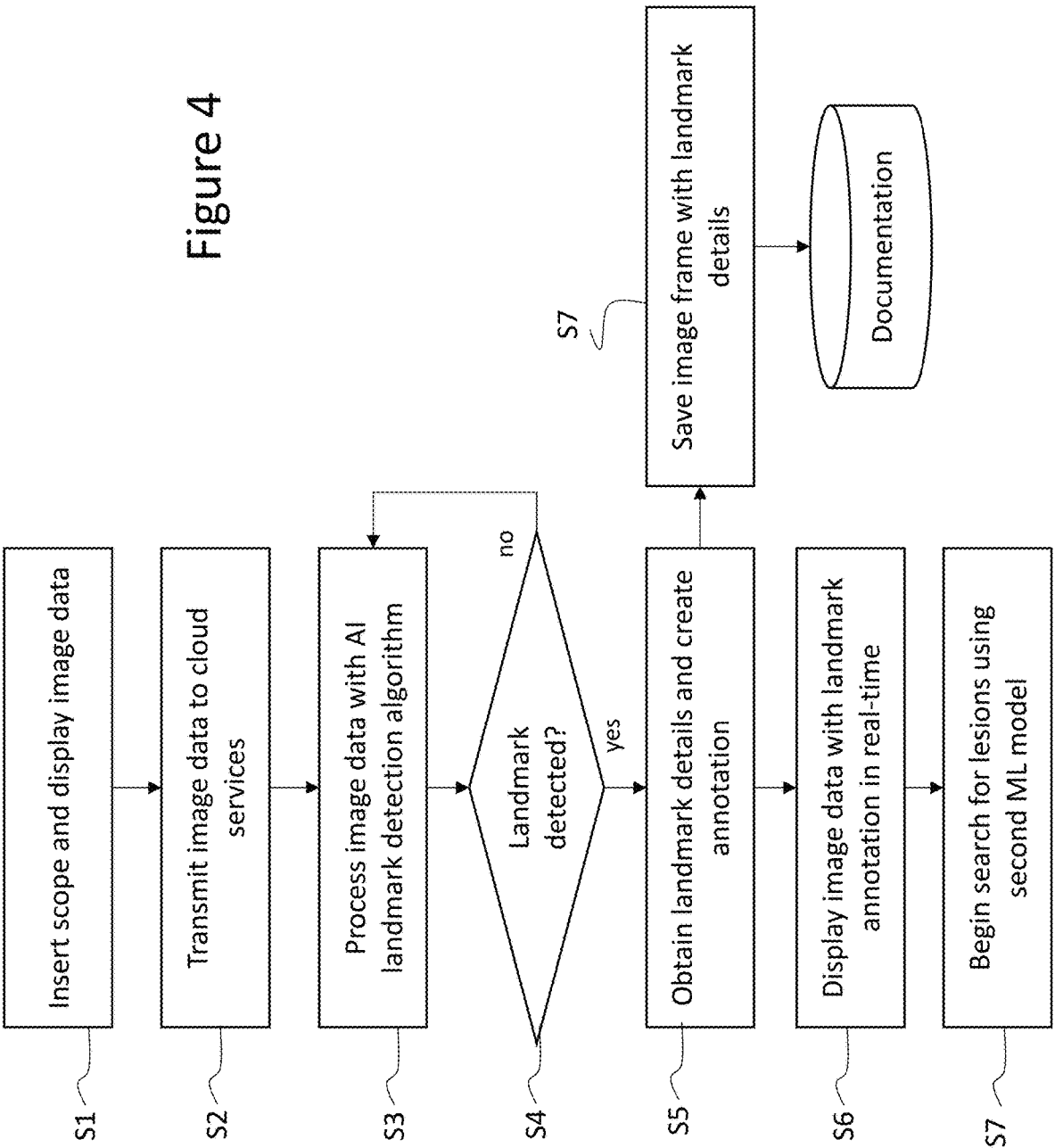

S1 — Insert scope and display image data

S2 — Transmit image data to cloud services

S3 — Process image data with AI landmark detection algorithm

S4 — Landmark detected?

no yes

S5 — Obtain landmark details and create annotation

S6 — Display image data with landmark annotation in real-time

S7 — Begin search for lesions using second ML model

S7 — Save image frame with landmark details

Documentation

MULTITHREADING VIDEO PROCESSING WITH CLOUD SERVICES TO DETECT AND ANALYZE LANDMARKS AND OBJECTS DURING A CLINICAL PROCEDURE

PRIORITY CLAIM

This continuation-in-part application claims priority to co-pending application Ser. No. 17/938,355 filed on Oct. 6, 2022, which is hereby incorporated by reference.

TECHNICAL FIELD

The subject matter of this disclosure relates to detecting and analyzing objects in a video feed, and more particularly relates to a multithreaded video processing system that utilizes cloud services to detect and analyze landmarks and lesions, and displays annotated video during a clinical procedure.

BACKGROUND

Identifying lesions, which are localized areas of tissue damage or abnormality, remains an important diagnostic challenge in the medical field. For example, colon polyps are a type of lesion that grow on the inner lining of the colon and are very common. Colon polyps are significant because they may be or may become malignant (cancerous). They also are important because based on their size, number, and microscopic anatomy (histology), a clinician can predict which patients are more likely to develop more polyps and colon cancer.

SUMMARY

Aspects of the disclosure provide a multithreaded video processing system that utilizes cloud services to detect and analyze landmarks and lesions, and outputs annotated video in real time during a clinical procedure.

A first aspect provides a system, comprising a memory and a processor coupled to the memory and configured to process a video stream captured during a clinical procedure according to process that includes: receiving and forwarding a current image frame from the video stream to a display manager using a first processing thread; forwarding the current image frame to a memory buffer; using a second processing thread that runs independently of the first processing thread to check for a new image frame in the memory buffer; in response to the new image frame being detected in the memory buffer, using the second processing thread to retrieve and forward the new image frame to a cloud service that is configured to detect lesions in image data; receiving a result from the cloud service at the second processing thread; in response to the result being indicative of a new detected lesion in the new image frame, performing object sizing on the new detected lesion using the second processing thread and forwarding new lesion information to the first processing thread; and receiving, at the first processing thread, the new lesion information and graphically overlaying the new lesion information onto the current image frame at the display manager.

A second aspect provides a method for processing a video stream captured during a clinical procedure, the method comprising: receiving and forwarding a current image frame from the video stream to a display manager using a first processing thread; forwarding the current image frame to a memory buffer; using a second processing thread that runs independently of the first processing thread to check for a new image frame in the memory buffer; in response to the new image frame being detected in the memory buffer, using the second processing thread to retrieve and forward the new image frame to a cloud service that is configured to detect lesions in image data; receiving a result from the cloud service at the second processing thread; in response to the result being indicative of a new detected lesion in the new image frame, performing object sizing on the new detected lesion using the second processing thread and forwarding new lesion information to the first processing thread; and receiving, at the first processing thread, the new lesion information and graphically overlaying the new lesion information onto the current image frame at the display manager.

A third aspect provides system, comprising a memory and a processor coupled to the memory and configured to process a video stream captured during a clinical procedure according to process that includes: receiving and forwarding a current image frame from the video stream to a display manager using a first processing thread; forwarding the current image frame to a memory buffer; using a second processing thread that runs independently of the first processing thread to check for a new image frame in the memory buffer; in response to the new image frame being detected in the memory buffer, using the second processing thread to retrieve and forward the new image frame to a cloud service that is configured to process image data; receiving a first result from the cloud service at the second processing thread; performing further image processing on the new image frame using the second processing thread to obtain a second result and forwarding the first and second result to the first processing thread; and receiving, at the first processing thread, the first and second result and graphically overlaying the first and second result onto the current image frame at the display manager.

A fourth aspect includes a system, comprising: a memory; and a processor coupled to the memory and configured to process a video stream captured during a clinical procedure according to process that includes: receiving and forwarding a current image frame from the video stream to a display manager using a first processing thread; forwarding the current image frame to a memory buffer; using a second processing thread that runs independently of the first processing thread to check for a new image frame in the memory buffer; in response to the new image frame being detected in the memory buffer, using the second processing thread to retrieve and forward the new image frame to a cloud service that is configured to identify landmarks in image data; receiving a result from the cloud service at the second processing thread; in response to the result being indicative of a new landmark in the new image frame, generating landmark annotations; and receiving, at the first processing thread, the landmark annotations and graphically overlaying the landmark annotations onto the current image frame at the display manager.

A fifth aspect includes a system, comprising: a memory; and a processor coupled to the memory and configured to process image data streamed from a scope during a clinical procedure according to process that includes: receiving and forwarding image data to a display as the scope is inserted into a patient; forwarding the image data to a cloud service that is configured to identify a landmark in the image data using a first machine learning model; receiving landmark details from the cloud service in response to a detected landmark and outputting the image data with landmark annotations via the display; receiving and forwarding further image data to the display as the scope is further manipulated within the patient; forwarding the further image data to a cloud service that is configured to detect lesions using a second machine learning model; and receiving lesion details from the cloud service in response to a detected lesion and outputting the further image data with lesion annotations via the display.

A sixth aspect includes a method, comprising: receiving image data streamed from a scope within a patient during a clinical procedure; forwarding the image data to a display as the scope is inserted into a patient; forwarding the image data to a cloud service that is configured to identify a landmark in the image data using a first machine learning model; receiving landmark details from the cloud service in response to a detected landmark and outputting the image data with landmark annotations via the display; receiving and forwarding further image data to the display as the scope is further manipulated within the patient; forwarding the further image data to a cloud service that is configured to detect lesions using a second machine learning model; and receiving lesion details from the cloud service in response to a detected lesion and outputting the further image data with lesion annotations via the display.

Additional aspects may include one or more of the following. A system and/or method wherein, prior to forwarding the current image frame to the memory buffer: determining whether the second processing thread is busy; and in response to determining that the second processing thread is busy, graphically overlaying previous lesion information onto the current image frame.

A system and/or method wherein, in response to determining that the second processing thread is not busy, converting the current frame to a JPEG format and loading current frame into the memory buffer. In further aspects, wherein, prior to forwarding the new image frame to the cloud service, encoding the new image frame to a Base64 format.

A system and/or method, wherein in response to the result from the cloud service not being indicative of a new detected lesion in the new image frame, causing the first processing thread to graphically overlaying previous lesion information onto the current image frame. In further aspects, the previous lesion information is obtained from the memory buffer.

A system and/or method, wherein forwarding new lesion information to the first processing thread includes: loading the new lesion information to the memory buffer by the second processing thread; and using the first processing thread to detect new lesion information in the memory buffer.

A system and/or method wherein the first processing thread and second processing run on separate CPU cores.

BRIEF DESCRIPTION OF THE DRAWINGS

These and other features of this invention will be more readily understood from the following detailed description of the various aspects of the invention taken in conjunction with the accompanying drawings in which:

FIG. 4 depicts a flow diagram of a process for detecting and processing landmarks according to embodiments.

Figure 1:
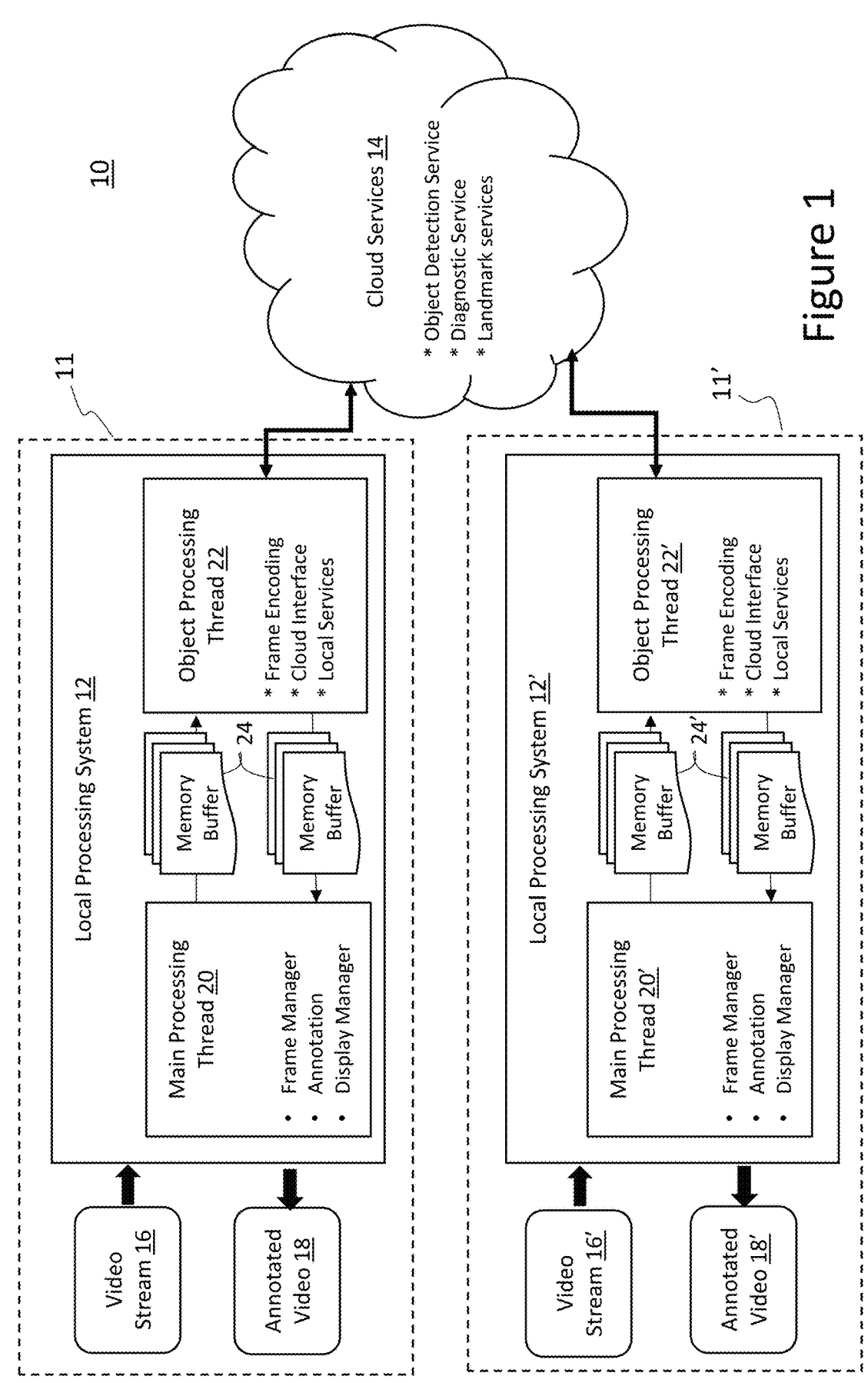
FIG. 1 shows a multithreading video processing platform with cloud services according to embodiments.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

Various embodiments provided herein relate to a computing infrastructure for processing a video feed to detect, size, and analyze objects and image data. In certain aspects, the video feed includes video displayed during a clinical scoping procedure, such as a colonoscopy, ureteroscopy, cystoscopy, bronchoscopy, etc. The video feed is outputted in real-time to a practitioner performing the procedure with annotations, e.g., landmark identification, lesion detection, size, histology, etc.

Various techniques exist for processing video feeds to provide such information. For example, U.S. Pat. No. 10,957,043 entitled AI Systems for Detecting and Sizing Lesions, which is hereby incorporated by reference, discloses machine learning techniques for detecting and sizing lesions, which can be displayed to the practitioner along with the video feed during a procedure. Technical challenges however arise due to the computational overhead required to implement such algorithms. When processing a video stream, traditional sequential computational techniques often cannot guarantee real-time results back to the practitioner. In order to address this issue, the present approach uses a distributed, multithreaded computing infrastructure to process and annotate video during the procedure.

Referring to FIG. 1, an illustrative computing infrastructure 10 is shown that processes video streams 16, 16', e.g., captured during procedures from different medical procedure rooms 11, 11' and outputs annotated video 18, 18' back to the medical practitioners performing the procedure. Video streams 16, 16' may be captured from a camera or scope used during the procedure and the resulting annotated video 18, 18' may be output on a display, such as a computer screen or the like. Each room 11, 11' includes a local processing system 12, 12' (or client) that includes: (1) a main (i.e., first) processing thread 20, 20' that handles the input, output and annotation of image frames; and (2) an object (i.e., second) processing thread 22, 22' for handling image processing tasks including the generation of annotation information. In addition, a set of cloud services 14, e.g., provided by a remote cloud system (i.e., server) are provided that perform one or more complex image processing tasks, e.g., object detection, diagnostics, etc., for each of the local processing systems 12, 12'.

In one illustrative embodiment, each local processing system 12, 12' includes a central processing unit (CPU) having multiple cores or a single core divided into multiple virtual cores (CPU cores) on which different threads can run.

Each thread is created by the operating system and performs a specific set of tasks. In certain aspects the main processing thread 20 runs on a first CPU core and the object processing thread 22 runs on a second CPU core independently of the first thread, i.e., the two threads operate at the same time independently of each other. In one illustrative embodiment, the main processing thread 20 provides input/output and the object processing annotation functions on the video stream 16, while object processing thread 22 manages cloud services 14 (which runs independently of both threads 20, 22) and performs further image processing tasks to generate annotation information. A memory buffer 24 may be deployed to buffer video frames or annotation information being transported between the two threads 20, 22. Using this multithreaded approach, various advantages are gained, e.g., if image processing gets bogged down in the object processing thread 22, it will not interfere with the main processing thread's 20 ability to display video to the practitioner.

Cloud services 14 include one or more functions that provide a further level of image processing. For example, computationally intensive processes such as object detection and diagnostics using machine learning algorithms or the like may be implemented by cloud services 14. Each cloud service 14 can be configured to perform a service in a highly efficient manner that manages computational overhead required for certain image processing tasks. An additional advantage of performing such specialized services on the cloud is that data from multiple rooms 11, 11' or sources can be collected at a single location and used for analytical purposes, e.g., to continuously train an associated machine learning model.

In certain aspects, cloud services 14 provides landmark identification that includes, e.g., detection, capture, and processing. Landmarks are specific anatomical points or features that serve as reference points for medical professionals during an imaging procedure. For example, during a gastrointestinal (GI) endoscopy procedure, landmarks act as visual cues to guide doctors, helping them navigate the different parts of the GI tract and identify potential issues. Upper GI landmarks may include the Z-line, gastric cardia, fundus, body, angulus, antrum, pylorus, and duodenal bulb. Lower GI landmarks may include the cecum, ileocecal valve, ascending colon, transverse colon, descending colon, sigmoid colon, and rectal area. Furthermore, various medical organizations have guidelines that call for images of certain landmarks to be captured and documented during an endoscopy. Accurate documentation of GI landmarks can be crucial for diagnosing abnormalities like ulcers, polyps, tumors, and inflammation, as well as for monitoring treatment progress and planning follow-up procedures.

Figure 2:
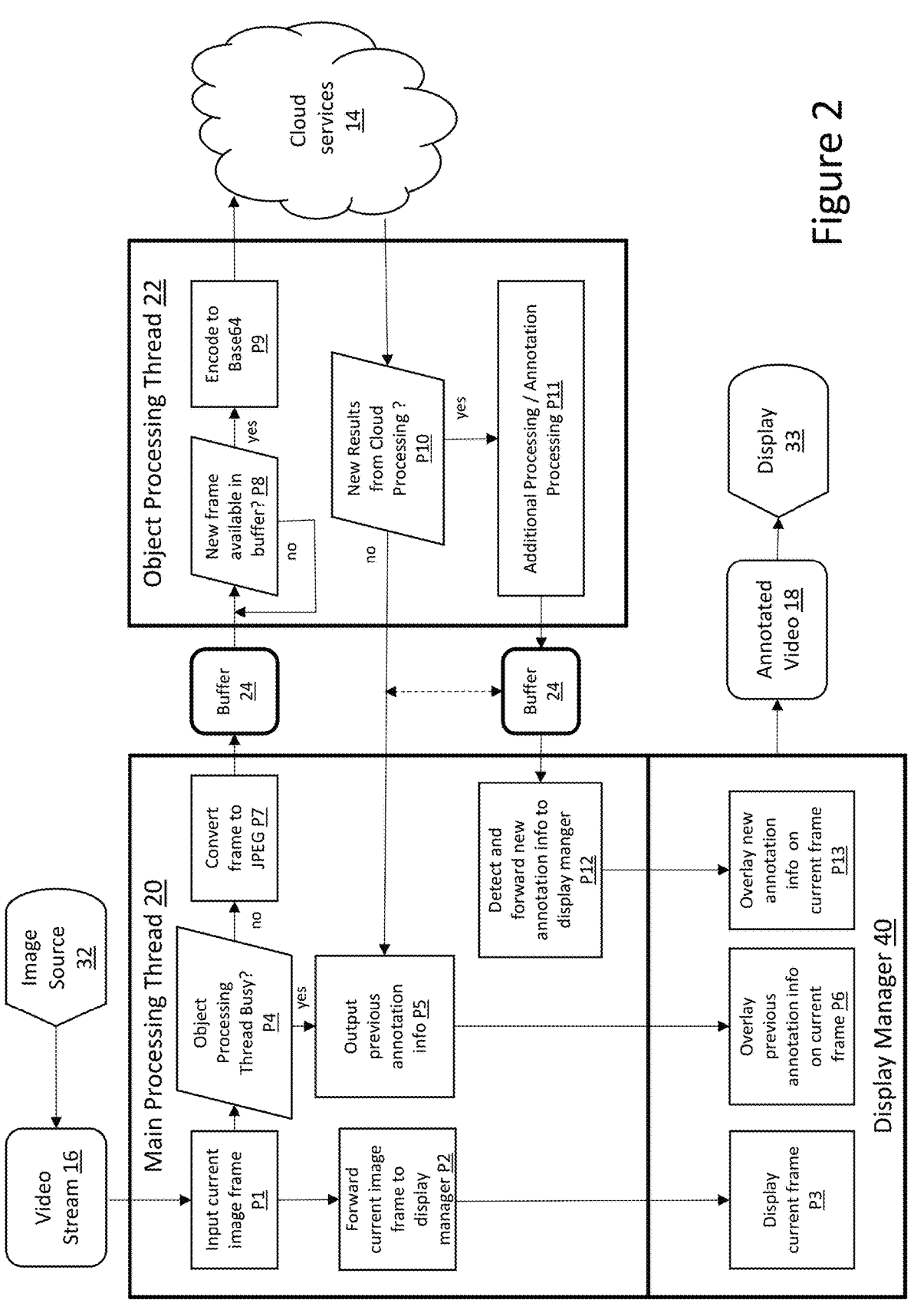
FIG. 2 shows details of a multithreading object detection and sizing process with cloud services according to embodiments.

FIG. 2 depicts a detailed process flow of a computing infrastructure that captures, processes, annotates, and outputs video in real-time during a procedure with, e.g., landmark details, lesion detection details, sizing information, diagnostics, etc. Annotated video (also referred to herein as annotations) 18 may for example include a graphically overlayed rectangle, oval, or other graphics indicia showing the location of a lesion and/or text data displaying information such as a diameter or histology of the detected lesion, landmark data, timing information, etc. In this embodiment, the main processing thread 20 receives a video stream 16 from an image source 32 (e.g., a camera, scope, etc.) that processes a sequence of image frames. In operation, a next, i.e., "current," image frame is inputted at P1, and at P2 the current image frame is forwarded to the display manager 40 (thus reproducing the inputted video stream 16) where the current image frame is rendered at P3 along with either previous annotation information (P6) or new annotation information (P13). A typical video stream 16 may for example include 32 frames per second that flow through the main processing thread 20 to the display manager 40. The resulting annotated video 18 is then output to a physical display 33. In an illustrative embodiment, the frames are in a BMP (bitmap image) file format.

Processes P4-P13 describe the functionality that adds annotations to each frame at the display manager 40. At P4, the main processing thread 20 determines if the object processing thread 22 is busy, e.g., processing a previous frame. If yes, thread 20 outputs previous annotation information, i.e., detection and size information determined for a previous frame at P5. This may also include retrieving previous raw annotation information from memory buffer 24, which can, e.g., include a collection of graphical data items that represent types and properties of graphical objects, e.g., rectangles, circles, and/or text. Drawing functions in the main processing thread 20 are used to, e.g., draw a frame and annotations (e.g., BMP data), based on the data in the buffer 24. The resulting graphics data is outputted to the display manager 40 (alternatively, the display manager 40 can simply be instructed to keep displaying the previous annotation information). At P6, display manager 40 graphically overlays (or simply keeps) previous annotation information on the current frame. Accordingly, this ensures that each displayed frame has relevant annotation information overlayed thereon, even if the object processing thread 22 is unable to provide new annotation information for the current frame.

If the object processing thread is not busy at P4, then the current frame is converted to a JPEG format at P7 and loaded to memory buffer 24 for processing by the object processing thread 22.

At P8, the object processing thread 22 checks to see if a new frame is available in the buffer 24. If no, process P8 waits until one is available. If a new frame is available, the JPEG image is encoded at P9, e.g., to Base64, which is a common encoding scheme for transporting images. The encoded image is then forwarded to cloud services 14 (which may include any type of server), where one or more image processing algorithms are applied to the image data.

Figure 3:
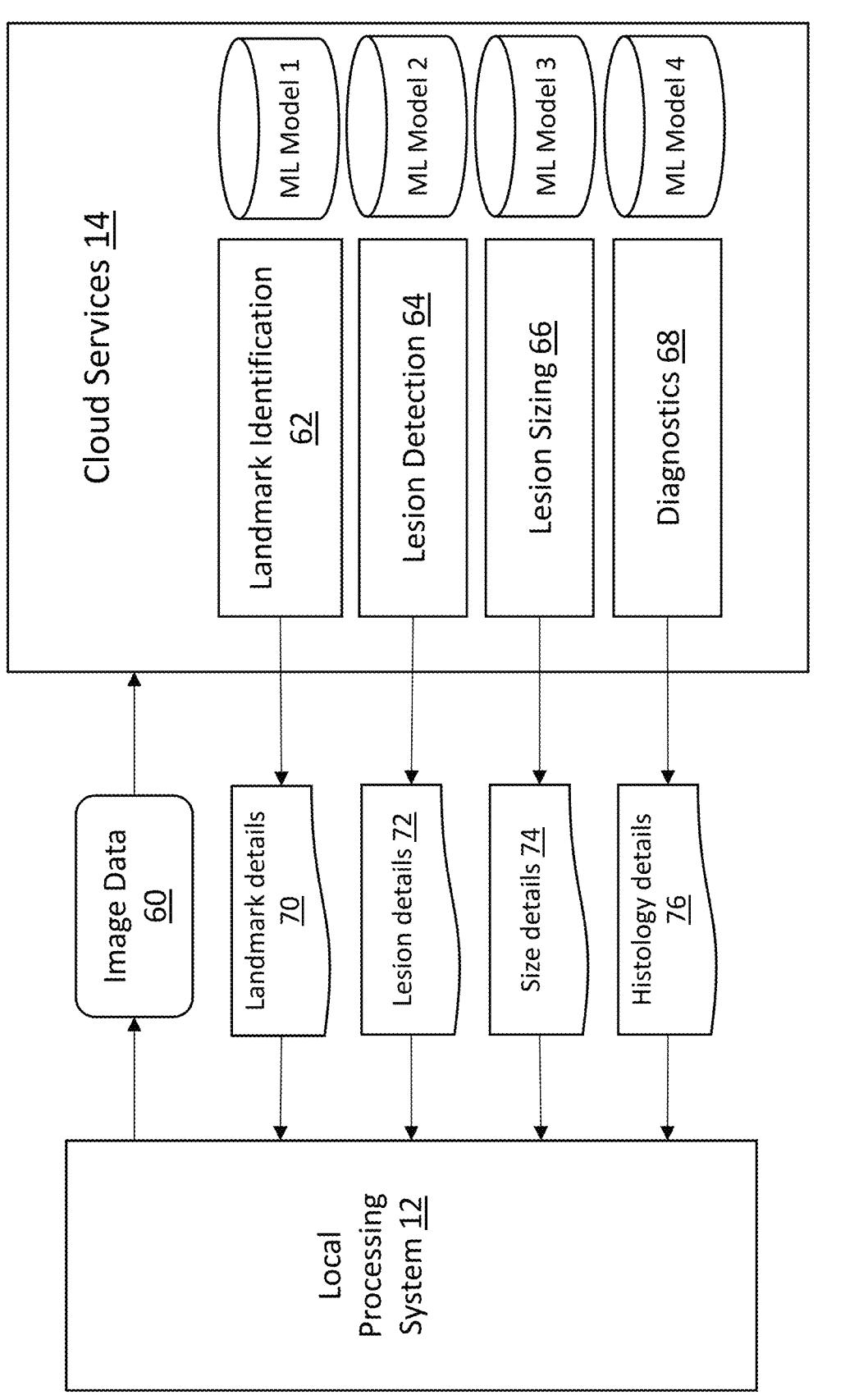
FIG. 3 cloud services and results for a local processing system according to embodiments.

FIG. 3 depicts an illustrative implementation of a local processing system 12 interfacing with cloud services 14 in which image data 60 (i.e., one or more image frames) are sent to cloud services 14 for processing. In this example, cloud services' algorithms include landmark identification 62, lesion detection 64, lesion sizing 66 and diagnostics 68. Each algorithm may for example include a machine learning (ML) model trained to perform an associated task. For example, landmark identification 62 may utilize ML model 1 that is trained on a large number of images that include one or more landmarks. In this case, the image data 60 is passed into ML model 1 (which may for example comprise a neural network) that predicts whether the image data 60 includes a landmark and/or what type of landmark. Similarly, lesion detection 64 may utilize ML model 2 that is trained on a large number of images that include lesions. Lesion sizing 66 may utilize ML model 3 that is trained on a large number of images that include a reference item (e.g., forceps, water jets, etc. of a known size). Diagnostic 68 may utilize ML model 4 that is trained on a large number of images with particular histologies. In some cases, ML models may be combined to perform more than one of the above algorithms, e.g., using a deep learning model. In various embodiments, cloud services 14 may implement some or all of the algorithms, and some may be implemented locally by local processing system 12.

As noted, identifying and documenting landmarks, which is performed by landmark identification 62, is a critical step in medical scoping procedures. For example, in certain endoscopy procedures, a doctor will insert an endoscope in the GI tract until the cecum is detected, and then begin extracting the scope to examine the tract. Landmark identification 62 can automatically detect the cecum and cause the displayed video to include an annotation (e.g., "cecum detected"), thereby simplifying the procedure for the doctor. In further cases, the annotations may include guidance information to the doctor based on detected landmarks (e.g., "begin scope extraction" or "procedure completed"). Landmark details 70, which may for example include a landmark identifier (e.g., a name, code, etc.) for a given image frame, are returned to the local processing system 12 than can then display/annotate image data 60 with landmark details 72. In other cases, detected landmarks can be linked to different frames in a video stream 16 for documentation and reporting purposes.

FIG. 4 depicts an illustrative cloud processing method involving landmark identification and lesion detection. At S1, a scope is inserted into a patient and image data is displayed to the doctor. At S2, the image data is transmitted to the cloud service 14 (e.g., using the system described in FIG. 2), and at S3, the image data is processed with an AI landmark detection algorithm using a first ML model. At S4, a determination is made whether a landmark is detected. If no landmark is detected, the process loops back to S3. If a landmark is detected, then landmark details are obtained from the cloud service and annotations are created at S5. At S6, the image data is displayed for the doctor with the landmark annotation in real-time. At S7, a second ML model is deployed to begin looking for lesions, e.g., as the scope is retracted from the detected landmark. Additionally, at S8, the image data (e.g., one or more frames) associated with a detected landmark is saved with landmark details, e.g., in a documentation database. (Although not shown, additional steps may include automated sizing and diagnosis as part of the process.) Accordingly, an automated process can be implemented to guide the doctor through a procedure based on landmark identification.

In certain embodiments, service 30 returns an XML file containing detection results (e.g., an identified landmark, a new lesion detected, no new lesion detected, location, etc.). Once the service 30 provides a result, process P10 determines if the result is a new result, i.e., a new landmark or lesion is detected. If no, then process P10 instructs the main processing thread 20 to use the previous annotation information at P5 for the current frame being displayed. If at P10 a new lesion detection result is detected by the object detection service 30 (indicative of a new lesion), then object sizing is performed either by another cloud service (lesion sizing 66) that returns size details 74 or by a local process at P11. Sizing of a lesion may likewise be performed using any known image processing technique. The resulting information (e.g., location, size, etc.) is packaged as a new set of annotation information and is loaded to memory buffer 24. As also noted in FIG. 3, cloud services 14 may include a diagnostics algorithm 68 that determines and returns histology details 76. Histology of a lesion may for example be determined in any manner, e.g., image analysis, sizing details, shape, color, etc. In an illustrative embodiment, various details from cloud services are returned as XML and is converted to graphical data when loaded into the buffer 24.

At P12, main processing thread 20 detects and forwards the new annotation information to the display manager 40. This may also include using drawing functions to convert annotation data in the buffer to graphics BMP data. At P13, the display manager 40 graphically overlays the new annotation information onto the current frame. The current frame and annotations are drawn simultaneously in the same thread, or the current frame is drawn along with the annotation from the previous frame.

Accordingly, each frame from the image source 32 is transported through the main processing thread 20 and is outputted as annotated video 18 to display 33 (e.g., a monitor in the procedure room). If the object processing thread 22 is available, an inputted BMP frame is converted to JPEG and sent through memory buffer 24 to the object processing thread 22, where it is encoded to Base64 and forwarded to the object detection service 30 on the cloud. The results come back as XML and are converted to a format supporting graphical annotation, and object sizing is performed. Finally, the results go back through the memory buffer 24 to the main processing thread 20, where new or previous annotation information is graphically overlayed with the current frame via the display manager 40.

If the object processing thread 22 is busy processing the last frame, the main processing thread 20 uses the annotation information of the previously analyzed frame from the memory buffer 24. In this case, the display manager 40 outputs visual annotation information for the previous frame on top of the current frame, and the result shows up on the monitor.

Figure 5:
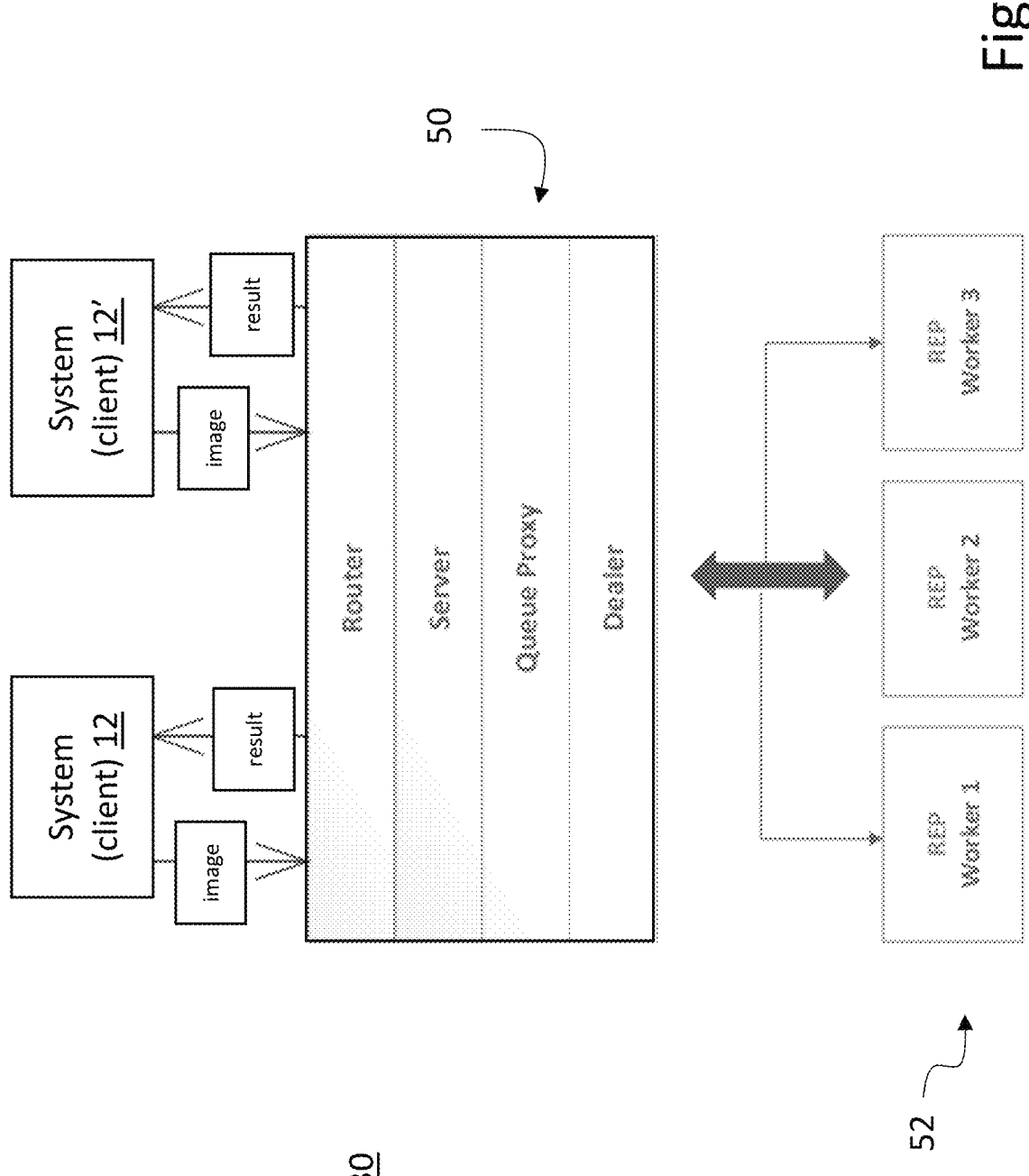
FIG. 5 shows a cloud services architecture according to embodiments.

FIG. 5 depicts an illustrative cloud service 14 implementation in which each of the various local processing systems 12, 12' (i.e., clients) interfaces with a router/server/queue proxy/dealer platform 50. Each client has a corresponding REP worker 52 in the cloud. In operation, the cloud server starts a set of worker threads. Each worker thread creates an REP socket and then processes requests on a socket. Each REP socket is used by the service to receive requests from and send replies to a client. This socket type allows an alternating sequence of receive and subsequent send calls. Each request received is fair-queued from among all clients, and each reply sent is routed to the client that issued the last request. Worker threads behave just like single-threaded servers. The only differences are the transport (inproc instead of tcp), and the bind-connect direction.

The server also creates a ROUTER socket to talk to clients and binds this to its external interface (e.g., over tcp). The server further creates a DEALER socket to talk to the workers and binds these to an internal interface (e.g., over inproc). The server also starts a proxy that connects the two sockets. The proxy pulls incoming requests from all clients and distributes those out to workers. It also routes replies to a corresponding client.

Each client uses the REQ socket to send requests and receive replies from a service running on the cloud server. This socket type allows only an alternating sequence of sends and subsequent receive calls. A REQ socket may be connected to n numbers of REP or ROUTER sockets. Each request sent is round-robin-ed among all connected services, and each reply is matched with the last issued request. If no services are available on the cloud server, any send operation on the socket will block until at least one service becomes available. The REQ socket will not discard any messages.

A REP socket is used by a service running on the cloud server to receive requests and send replies to a client. This socket type allows only an alternating receive and subsequent send calls sequence. Each request received is queued from among all clients, and each reply sent is routed to the client that issued the last request. If the original requester does not exist anymore, the response is silently discarded.

A DEALER socket type talks to a set of anonymous peers, sending and receiving messages using round-robin algorithms. The DEALER works as an asynchronous REQ replacement for clients who talk to REP or ROUTER servers. The messages received by a DEALER are queued from all connected peers.

The ROUTER socket type talks to a set of peers, using explicit addressing to send each outgoing message to a specific peer connection. ROUTER works as an asynchronous replacement for REP and is often used as the basis for servers that talk to DEALER clients.

Figure 7:
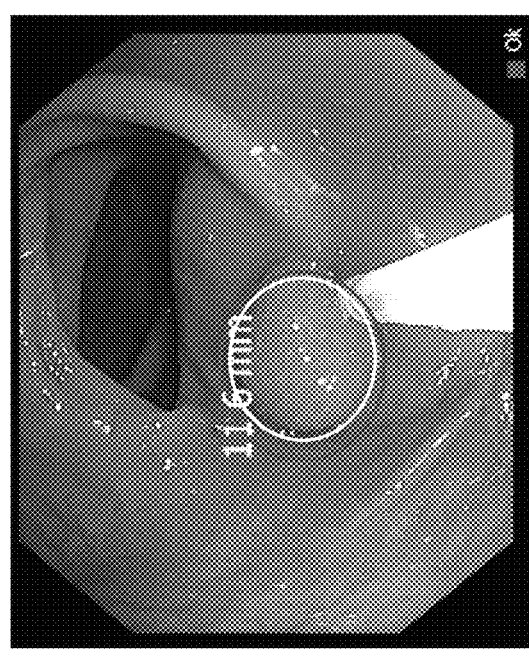
FIG. 7 shows an annotated image with sizing details according to embodiments.
Figure 8:
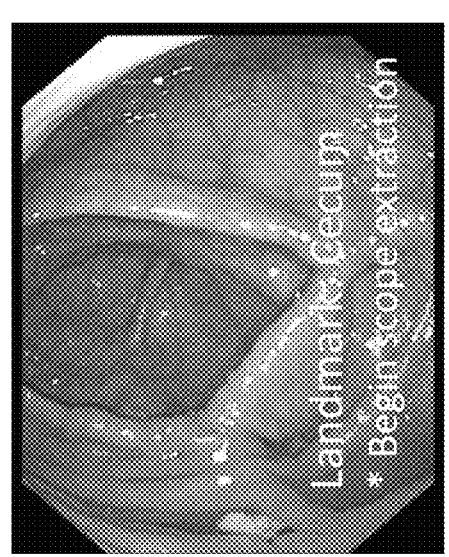
FIG. 8 shows an annotated image with landmark details according to embodiments.
Figure 6:
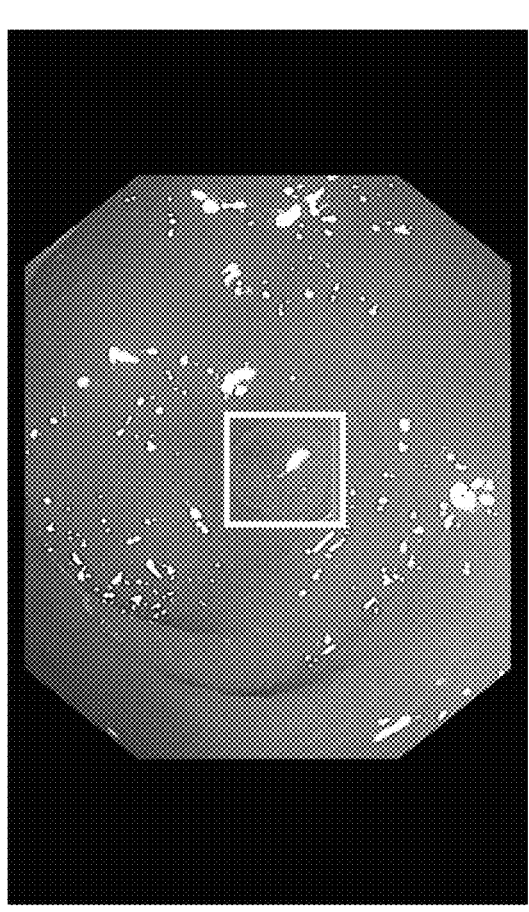
FIG. 6 shows an image with a polyp detection result according to embodiments.

FIG. 6 depicts an illustrative annotated frame showing the results of a lesion detection. This image depicts a detected polyp inside the square. FIG. 7 depicts an illustrative annotated frame showing sizing information of a detected polyp. In this case, the polyp is encircled in an oval and is shown to be 11.6 mm in diameter. FIG. 8 shows annotated image data showing a landmark annotation (Cecum). In this case, guidance is also displayed to the doctor (i.e., begin scope extraction).

Figure 9:
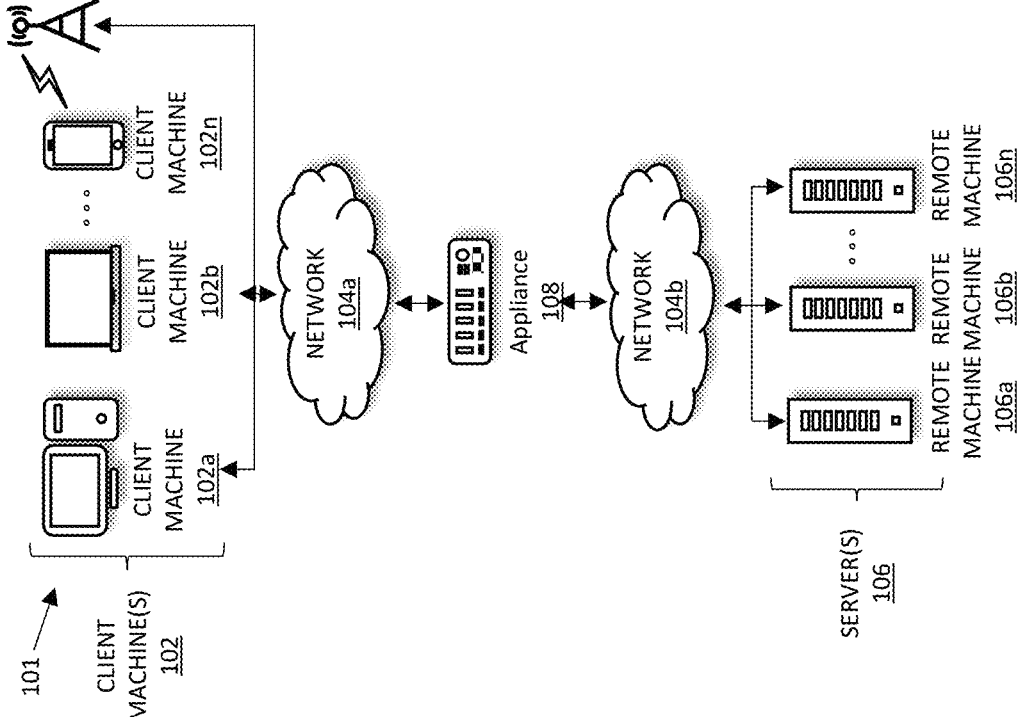
FIG. 9 depicts a network, according to embodiments.

It is understood that aspects of the described video processing infrastructure can be implemented in any manner, e.g., as a stand-alone system, a distributed system, within a network environment, etc. Referring to FIG. 9, a non-limiting network environment 101 in which various aspects of the disclosure may be implemented includes one or more client machines 102A-102N, one or more remote machines 106A-106N, one or more networks 104, 104', and one or more appliances 108 installed within the computing environment 101. The client machines 102A-102N communicate with the remote machines 106A-106N via the networks 104, 104'.

In some embodiments, the client machines 102A-102N communicate with the remote machines 106A-106N via an intermediary appliance 108. The illustrated appliance 108 is positioned between the networks 104, 104' and may also be referred to as a network interface or gateway. In some embodiments, the appliance 108 may operate as an application delivery controller (ADC) to provide clients with access to business applications and other data deployed in a datacenter, the cloud, or delivered as Software as a Service (SaaS) across a range of client devices, and/or provide other functionality such as load balancing, etc. In some embodiments, multiple appliances 108 may be used, and the appliance(s) 108 may be deployed as part of the network 104 and/or 104'.

The client machines 102A-102N may be generally referred to as client machines 102, local machines 102, clients 102, client nodes 102, client computers 102, client devices 102, computing devices 102, endpoints 102, or endpoint nodes 102. The remote machines 106A-106N may be generally referred to as servers 106 or a server farm 106. In some embodiments, a client device 102 may have the capacity to function as both a client node seeking access to resources provided by a server 106 and as a server 106 providing access to hosted resources for other client devices 102A-102N. The networks 104, 104' may be generally referred to as a network 104. The networks 104 may be configured in any combination of wired and wireless networks.

A server 106 may be any server type such as, for example: a file server; an application server; a web server; a proxy server; an appliance; a network appliance; a gateway; an application gateway; a gateway server; a virtualization server; a deployment server; a Secure Sockets Layer Virtual Private Network (SSL VPN) server; a firewall; a web server; a server executing an active directory; a cloud server; or a server executing an application acceleration program that provides firewall functionality, application functionality, or load balancing functionality.

A server 106 may execute, operate or otherwise provide an application that may be any one of the following: software; a program; executable instructions; a virtual machine; a hypervisor; a web browser; a web-based client; a client-server application; a thin-client computing client; an ActiveX control; a Java applet; software related to voice over internet protocol (VOIP) communications like a soft IP telephone; an application for streaming video and/or audio; an application for facilitating real-time-data communications; a HTTP client; a FTP client; an Oscar client; a Telnet client; or any other set of executable instructions.

In some embodiments, a server 106 may execute a remote presentation services program or other program that uses a thin-client or a remote-display protocol to capture display output generated by an application executing on a server 106 and transmit the application display output to a client device 102.

In yet other embodiments, a server 106 may execute a virtual machine providing, to a user of a client device 102, access to a computing environment. The client device 102 may be a virtual machine. The virtual machine may be managed by, for example, a hypervisor, a virtual machine manager (VMM), or any other hardware virtualization technique within the server 106.

In some embodiments, the network 104 may be: a local-area network (LAN); a metropolitan area network (MAN); a wide area network (WAN); a primary public network 104; and a primary private network 104. Additional embodiments may include a network 104 of mobile telephone networks that use various protocols to communicate among mobile devices. For short range communications within a wireless local-area network (WLAN), the protocols may include 802.11, Bluetooth, and Near Field Communication (NFC).

Figure 10:
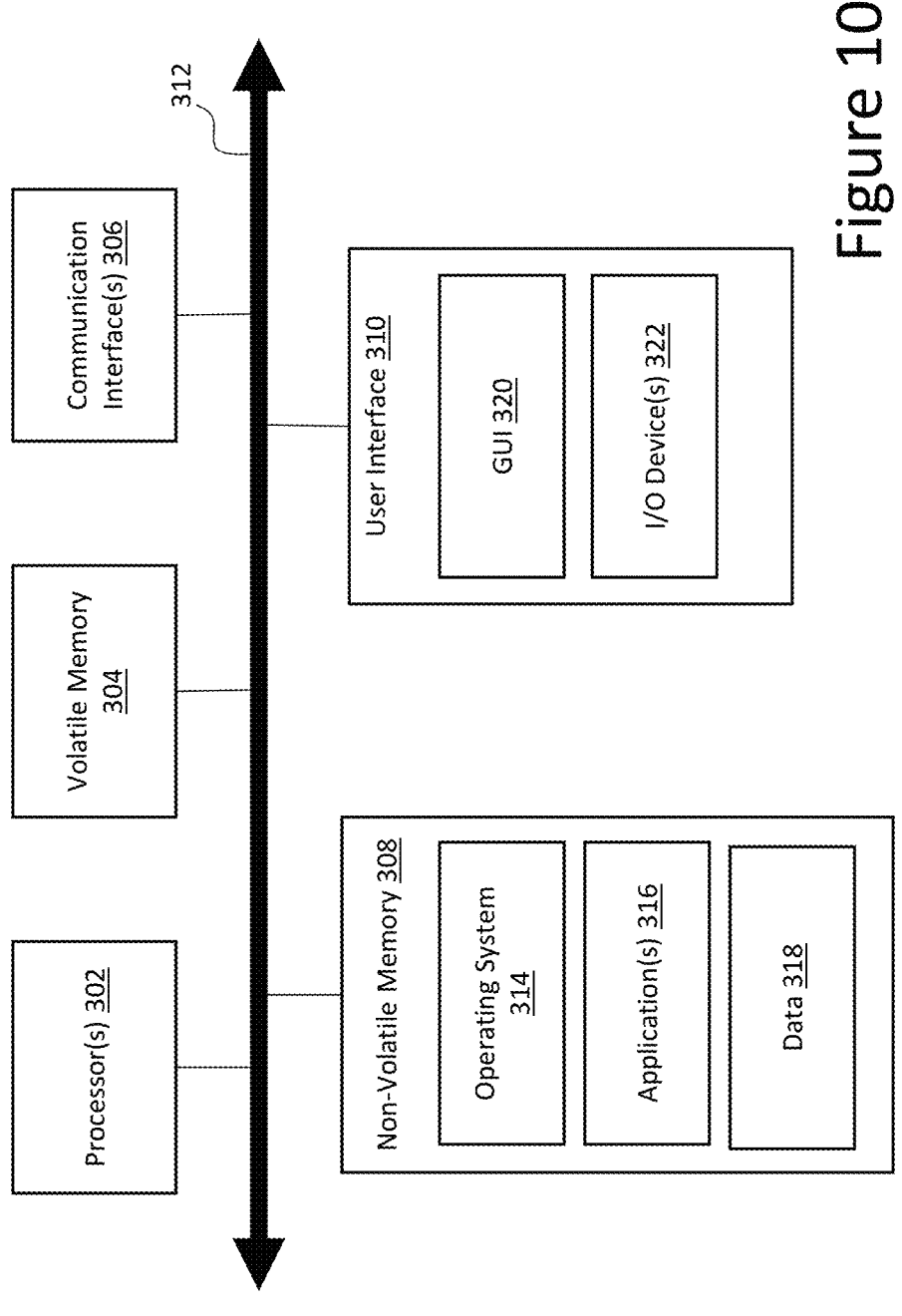
FIG. 10 depicts a computer system, according to embodiments.

Elements of the described solution may be embodied in a computing system, such as that shown in FIG. 10 in which a computing device 300 may include one or more processors 302, volatile memory 304 (e.g., RAM), non-volatile memory 308 (e.g., one or more hard disk drives (HDDs) or other magnetic or optical storage media, one or more solid state drives (SSDs) such as a flash drive or other solid state storage media, one or more hybrid magnetic and solid state drives, and/or one or more virtual storage volumes, such as a cloud storage, or a combination of such physical storage volumes and virtual storage volumes or arrays thereof), user interface (UI) 310, one or more communications interfaces 306, and communication bus 312. User interface 310 may include graphical user interface (GUI) 320 (e.g., a touchscreen, a display, etc.) and one or more input/output (I/O) devices 322 (e.g., a mouse, a keyboard, etc.). Non-volatile memory 308 stores operating system 314, one or more applications 316, and data 318 such that, for example, computer instructions of operating system 314 and/or applications 316 are executed by processor(s) 302 out of volatile memory 304. Data may be entered using an input device of GUI 320 or received from I/O device(s) 322. Various elements of computer 300 may communicate via communication bus 312. Computer 300 as shown in FIG. 10 is shown merely as an example, as clients, servers and/or appliances and may be implemented by any computing or processing environment and with any type of machine or set of machines that may have suitable hardware and/or software capable of operating as described herein.

Processor(s) 302 may be implemented by one or more programmable processors executing one or more computer programs to perform the functions of the system. As used herein, the term "processor" describes an electronic circuit that performs a function, an operation, or a sequence of operations. The function, operation, or sequence of operations may be hard coded into the electronic circuit or soft coded by way of instructions held in a memory device. A "processor" may perform the function, operation, or sequence of operations using digital values or using analog signals. In some embodiments, the "processor" can be embodied in one or more application specific integrated circuits (ASICs), microprocessors, digital signal processors, microcontrollers, field programmable gate arrays (FPGAs), programmable logic arrays (PLAs), multi-core processors, or general-purpose computers with associated memory. The "processor" may be analog, digital or mixed-signal. In some embodiments, the "processor" may be one or more physical processors or one or more "virtual" (e.g., remotely located or "cloud") processors.

Communications interfaces 306 may include one or more interfaces to enable computer 300 to access a computer network such as a LAN, a WAN, or the Internet through a variety of wired and/or wireless or cellular connections.

In described embodiments, a first computing device 300 may execute an application on behalf of a user of a client computing device (e.g., a client), may execute a virtual machine, which provides an execution session within which applications execute on behalf of a user or a client computing device (e.g., a client), such as a hosted desktop session, may execute a terminal services session to provide a hosted desktop environment, or may provide access to a computing environment including one or more of: one or more applications, one or more desktop applications, and one or more desktop sessions in which one or more applications may execute.

As will be appreciated by one of skill in the art upon reading the following disclosure, various aspects described herein may be embodied as a system, a device, a method or a computer program product (e.g., a non-transitory computer-readable medium having computer executable instruction for performing the noted operations or steps). Accordingly, those aspects may take the form of an entirely hardware embodiment, an entirely software embodiment, or an embodiment combining software and hardware aspects. Furthermore, such aspects may take the form of a computer program product stored by one or more computer-readable storage media having computer-readable program code, or instructions, embodied in or on the storage media. Any suitable computer readable storage media may be utilized, including hard disks, CD-ROMs, optical storage devices, magnetic storage devices, and/or any combination thereof.

The foregoing drawings show some of the processing associated according to several embodiments of this disclosure. In this regard, each drawing or block within a flow diagram of the drawings represents a process associated with embodiments of the method described. It should also be noted that in some alternative implementations, the acts noted in the drawings or blocks may occur out of the order noted in the figure or, for example, may in fact be executed substantially concurrently or in the reverse order, depending upon the act involved. Also, one of ordinary skill in the art will recognize that additional blocks that describe the processing may be added.

What is claimed is:

1. A system, comprising:
   a computing infrastructure for processing video streams simultaneously captured from a plurality of medical procedure rooms, the computing infrastructure having a plurality of local processing systems, each configured to support one of the plurality of medical procedure rooms, wherein each local processing system is networked to a shared cloud service via a set of REP sockets that receive requests in a round-robin fashion and wherein each REP socket only allows alternating requests and replies, and wherein each local processing system includes:
   a memory; and
   a processor coupled to the memory and configured to process a video stream captured during a clinical procedure according to process that includes:
      receiving and forwarding a current image frame from the video stream to a display manager using a first processing thread;
      forwarding the current image frame to a memory buffer;
      using a second processing thread that runs independently of the first processing thread to check for a new image frame in the memory buffer;
      in response to the new image frame being detected in the memory buffer, using the second processing thread to retrieve and forward a request containing the new image frame to a selected REP socket in the shared cloud service that is configured to identify landmarks in image data, wherein each of the landmarks comprises a specific anatomical feature in a normal gastrointestinal tract that serves as a reference point for the clinical procedure;
      receiving a reply from the selected REP socket containing a result from the cloud service at the second processing thread;
      in response to the result being indicative of a new landmark in the new image frame, generating landmark annotations; and
      receiving, at the first processing thread, the landmark annotations and graphically overlaying the landmark annotations onto the current image frame at the display manager.

2. The system of claim 1, wherein each local processing system uses a REQ socket to send requests to an available REP socket on the shared cloud service, wherein the REQ socket will be blocked from sending the request if no REP sockets are available, and wherein the REQ socket will hold the request until a REQ socket becomes available.

3. The system of claim 2, wherein, in response to determining that the second processing thread is not busy, converting the current image frame to a JPEG format and loading current image frame into the memory buffer.

4. The system of claim 1, wherein the new landmark comprises one of a Z-line, gastric cardia, fundus, body, angulus, antrum, pylorus, duodenal bulb, cecum, ileocecal valve, ascending colon, transverse colon, descending colon, sigmoid colon, and rectum.

5. The system of claim 1, wherein in response to the result from the cloud service not being indicative of a new landmark in the new image frame, causing the first processing thread to graphically overlay previous landmark annotations onto the current image frame.

6. The system of claim 5, wherein the previous landmark annotations are obtained from the memory buffer.

7. The system of claim 1, wherein forwarding new landmark annotations to the first processing thread includes:

loading the new landmark annotations to the memory buffer by the second processing thread; and using the first processing thread to detect new landmark annotations in the memory buffer.

8. The system of claim 1, wherein the first processing thread and second processing run on separate central processing unit (CPU) cores, which are separate from the cloud service.

9. A system, comprising:

a computing infrastructure for processing video streams simultaneously captured from a plurality of medical procedure rooms, the computing infrastructure having a plurality of local processing systems, each configured to support one of the plurality of medical procedure rooms, wherein each local processing system is networked to a shared cloud service via a set of REP sockets that receive requests in a round-robin fashion and wherein each REP socket only allows alternating requests and replies, and wherein each local processing system includes:

a memory; and a processor coupled to the memory and configured to process image data streamed from a scope during a clinical procedure according to process that includes:

receiving and forwarding image data to a display as the scope is inserted into a patient;

forwarding the image data to a first selected REP socket in the shared cloud service that is configured to identify a landmark in the image data using a first machine learning model, wherein the landmark comprises a specific anatomical feature that serves as a reference point during the clinical procedure;

receiving landmark details from the first selected REP socket in the shared cloud service in response to a detected landmark and outputting the image data with landmark annotations via the display;

receiving and forwarding further image data to the display as the scope is further manipulated within the patient;

forwarding the further image data to a second selected REP socket in the cloud service that is configured to detect lesions using a second machine learning model; and receiving lesion details from the second selected cloud service in response to a detected lesion and outputting the further image data with lesion annotations via the display.

10. The system of claim 9, wherein each local processing system uses a REQ socket to send requests to an available REP socket on the shared cloud service, wherein the REQ socket will be blocked from sending the request if no REP sockets are available, and wherein the REQ socket will hold the request until a REQ socket becomes available.

11. The system of claim 9, wherein outputting of the image data with landmark annotations and further image data with lesion annotations occurs while the scope is within the patient.

12. The system of claim 9, wherein:

receiving and forwarding image data and further image data to the display is implemented with a first processing thread; and forwarding the image data and further image data to a cloud service is implemented with a second processing thread.

13. The system of claim 12, wherein the first processing thread runs on a first central processing unit (CPU) core and the second processing thread runs on a second CPU core, and wherein the first and second CPU cores are independent of the cloud service.

14. The system of claim 9, wherein the procedure comprises a gastrointestinal procedure and the landmark comprises a cecum.

15. The system of claim 9, wherein in response to the detected lesion, utilizing a third machine learning model to size the lesion.

16. The system of claim 15, wherein in response to the detected lesion, utilizing a fourth machine learning model to diagnose the lesion.

17. A method, comprising:

simultaneously processing video streams captured from a plurality of medical procedure rooms with a plurality of local processing systems, wherein each local processing system is networked to a shared cloud service via a set of REP sockets that receive requests in a round-robin fashion and wherein each REP socket only allows alternating requests and replies, and wherein each local processing system includes:

receiving image data streamed from a scope at a first local processing system during a clinical procedure;

forwarding the image data to a display as the scope is inserted into a patient;

forwarding the image data to a first selected REP socket at the shared cloud service that is configured to identify a landmark in the image data using a first machine learning model, wherein the landmark comprises a specific anatomical feature that serves as a reference point during the clinical procedure;

receiving landmark details from the first selected REP socket at the shared cloud service in response to a detected landmark and outputting the image data with landmark annotations via the display;

receiving and forwarding further image data to the display as the scope is further manipulated within the patient;

forwarding the further image data to a second selected REP socket at the shared cloud service that is configured to detect lesions using a second machine learning model; and receiving lesion details from the second selected shared cloud service in response to a detected lesion and outputting the further image data with lesion annotations via the display.

18. The method of claim 17, wherein the procedure comprises a gastrointestinal procedure and the landmark comprises a cecum, and wherein further manipulation of the scope within the patient comprises a retraction of the scope.

19. The method of claim 17, wherein:

receiving and forwarding image data and further image data to the display is implemented with a first processing thread; and forwarding the image data and further image data to a cloud service is implemented with a second processing thread.

20. The method of claim 19, wherein the first processing thread runs on a first central processing unit (CPU) core and the second processing thread runs on a second CPU core, and wherein the first and second CPU cores are independent of the cloud service.

* * * * *